United States Patent
Ricol

(10) Patent No.: US 8,377,014 B2
(45) Date of Patent: Feb. 19, 2013

(54) IMPLANTABLE SITE WITH A CASING HAVING MULTIPLE PERFORATIONS

(75) Inventor: Jean-Paul Ricol, Lyons (FR)

(73) Assignee: Compagnie Europeenne d'Etude et de Recherche de Depositifs pour l'Implantation par Laparoscopie, Vienne (FR)

( * ) Notice: Subject to any disclaimer, the term of this patent is extended or adjusted under 35 U.S.C. 154(b) by 0 days.

(21) Appl. No.: 13/119,627

(22) PCT Filed: Sep. 17, 2009

(86) PCT No.: PCT/EP2009/062047
§ 371 (c)(1),
(2), (4) Date: Mar. 17, 2011

(87) PCT Pub. No.: WO2010/031811
PCT Pub. Date: Mar. 25, 2010

(65) Prior Publication Data
US 2011/0166534 A1   Jul. 7, 2011

(30) Foreign Application Priority Data

Sep. 18, 2008  (FR) ..................................... 08 05145

(51) Int. Cl.
*A61M 11/00* (2006.01)
(52) U.S. Cl. .......... 604/288.02; 604/288.01; 604/288.04

(58) Field of Classification Search ............. 604/288.01, 604/288.02, 288.04
See application file for complete search history.

(56) References Cited

U.S. PATENT DOCUMENTS

| 5,328,465 A * | 7/1994 | Kratoska et al. ......... 604/288.02 |
| 7,985,207 B2 * | 7/2011 | Paganon ................. 604/288.02 |

FOREIGN PATENT DOCUMENTS

| FR | 2 877 582 | 5/2006 |
| FR | 2 905 603 | 3/2008 |
| FR | 2 913 203 | 9/2008 |
| WO | WO 2006/021695 | 3/2006 |
| WO | WO 2006051192 A1 * | 5/2006 |

* cited by examiner

*Primary Examiner* — Laura Bouchelle
(74) *Attorney, Agent, or Firm* — Occhiuti Rohlicek & Tsao LLP

(57) ABSTRACT

The invention relates to an implantable medical device for injecting and/or collecting fluid substance into and/or from a human or animal organism, said device comprising a casing (6) whose wall (3) delimits a chamber and is pierced with at least a first access orifice (7) designed to allow a needle to pass through said wall (3), said device being characterized in that the first access orifice has a staged structure comprising: a guide portion designed to limit the angular clearance of the needle when said needle is engaged therein, and a flared intake portion that forms a continuation of the guide portion, so as to be able to cause the trajectory of the incoming needle to converge on the guide portion. Implantable medical devices.

16 Claims, 2 Drawing Sheets

COUPE B-B

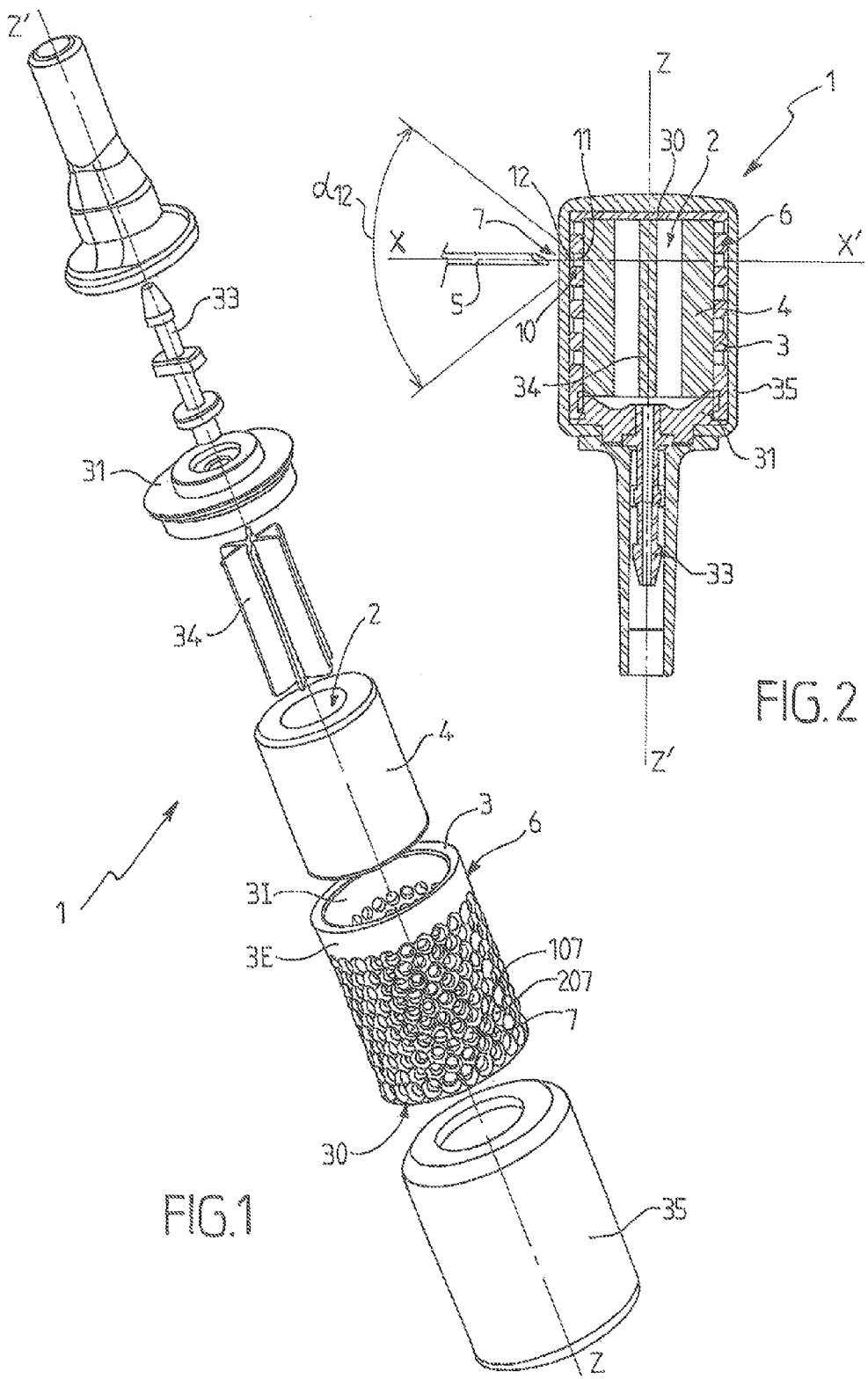

COUPE A-A  COUPE B-B

COUPE C-C

IMPLANTABLE SITE WITH A CASING HAVING MULTIPLE PERFORATIONS

CROSS REFERENCE TO RELATED APPLICATIONS

This application is the national stage entry under 35 USC 371 for: PCT/EP2009/062047, filed on Sep. 17, 2009, which claims the benefit of the Sep. 18, 2008 priority date of French application 0805145. The contents of both the foregoing applications are incorporated herein by reference.

The invention relates to implantable medical devices for injecting and/or collecting fluid substances into and/or from a patient's body, these devices being known as "implantable sites".

The present invention pertains more particularly to an implantable medical device designed for injecting and/or collecting fluid substance into and/or from a human or animal organism, said device comprising a casing, the wall of which demarcates a chamber designed to receive said fluid substance, the wall of the casing being pierced with at least one first access orifice positioned so as to enable a needle, designed to inject fluid substance into the chamber or collect fluid substance from the chamber, to go through said wall in crossing said first access orifice.

There are known ways of implanting a medical device called an "implantable site" beneath a patient's skin, this device being designed to form a remote point of access enabling the transfer of substances to or from the blood circulation system, the tissues of an organ or again, an inflatable implant such as a balloon or a constriction ring.

Generally, an implantable site of this kind takes the form of a casing in which a chamber is made, this chamber communicating with a flexible catheter connecting said casing to the target area for which the injected substance is intended, or from which the collected substance comes.

In order to allow access to the chamber by a hollow needle, the wall of the casing generally has a removal area formed by a self-sealing membrane or "septum" made out of an elastomer so that the imperviousness or tight sealing quality of the site is preserved both when the needle pierces the wall and when the needle is withdrawn from the wall, the hole formed by said needle automatically closing, when the needle is extracted, by a phenomenon of elastic self-healing.

Although they give appreciable results in facilitating the operations of injection and removal, the prior-art implantable sites sometimes have non-negligible drawbacks.

In the first place, the prior-art sites are generally provided with self-sealing membranes that are relatively thick in order to ensure the imperviousness of the chamber even after a large number of piercing operations. Said membranes therefore put up a major force of resistance against the needle during penetration, and this force exposes said needles to bending by buckling.

Furthermore, once the needle is engaged in the septum, its path is appreciably captive, i.e. it cannot be deflected except by twisting the needle. Now it sometimes happens that the needle, because of its particular angle of penetration, remains trapped in the thickness of the septum or again prematurely abuts a wall of the casing without sufficiently reaching the interior of the chamber to ensure the transfer of fluid substance. Naturally, such incidents compromise the efficiency of the therapeutic treatment and entail a repetition of the injection gesture giving rise to discomfort or even unnecessary suffering on the part of the patient.

Finally, the prior-art septums often have a useful surface area and an accessibility that are relatively restricted as compared with the overall space taken up by the implantable site.

The objects assigned to the present invention consequently aim at overcoming the above-mentioned drawbacks and proposing a novel implantable medical device designed for the injection and/or collection of fluid substance into and/or from a human or animal organism, this device having high accessibility and improved reliability of operation.

Another object assigned to the invention is aimed at proposing a novel implantable medical device that has longevity and reinforced imperviousness.

Another object assigned to the invention is aimed at proposing a novel atraumatic implantable medical device that minimizes the discomfort caused to the patient.

Another object assigned to the invention is aimed at proposing a novel implantable medical device with a particularly simple and compact structure.

Another object assigned to the invention proposes a novel implantable medical device which costs little to manufacture, is simple to assemble and is particularly tolerant to heterogeneities in the manufacture of its different components.

The objects assigned to the invention are achieved by means of an implantable medical device for injecting and/or removing a fluid substance into and/or from a human or animal organism, said device comprising a casing whose wall demarcates a chamber designed to receive said fluid substance, the wall of the casing being pierced with at least one first access orifice positioned to enable a needle designed for injecting or removing the fluid substance into or from the chamber to go through said wall in crossing said first access orifice, the device being characterized in that the first access orifice has a staged structure comprising:

a guiding portion designed to limit the angular play of the needle when said needle is engaged therein, around a predetermined reference direction of penetration (XX') oriented towards the chamber, a flared intake portion that extends the guiding portion and opens on to the external surface of the wall so that it can make the path of the incident needle converge towards the guiding portion and enable the engagement of said needle in said guiding portion.

Other objects and characteristics of the invention shall appear in greater detail from the following description as well as from the appended drawings, provided by way of a purely illustrative and non-exhaustive example, of which:

FIG. 1 is an exploded view in perspective of a first embodiment of the implantable medical device according to the invention.

FIG. 2 provides an illustration, in a longitudinal sectional view of the medical device of FIG. 1 in assembled configuration.

Figures 8, 9:
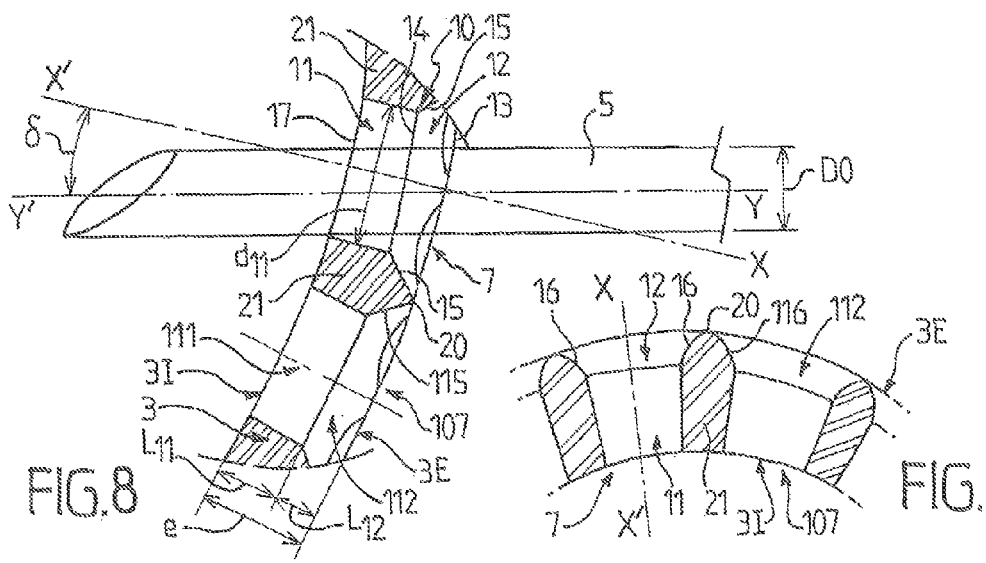

FIG. 9 provides an illustration in a schematic detailed view in cross-section of an alternative embodiment of the casing according to the invention.

The invention pertains to an implantable medical device 1 for injecting and/or removing fluid substances into or from a human or animal organism.

Such a device 1, also called an "implantable site", is designed to be implanted surgically in a patient's body, preferably beneath said patient's skin in order to constitute a point of access for introducing or extracting fluid substances into or from the patient's body.

The device 1 can be implemented and adapted to various uses.

In particular, the device 1 of the invention may be designed for injecting and/or collecting fluid into or from an organ or the circulatory system, for example to enable the injection of medicinal substances. According to one particular variant of this application, said device 1 may be adapted to forming an artificial vein or artery which the practitioner can pierce through the skin as with a natural vein in order to inject a therapeutic substance or collect blood.

The device 1 of the invention can also be adapted to feeding implanted reservoirs, associated for example with insulin or antalgic pumps.

Said device 1 can finally be adapted to injecting and removing fluid into and from the inflatable compartment of a surgical implant such as an artificial sphincter, a balloon or again a gastric ring designed to constrict the stomach in order to combat obesity.

Here below, the device 1 shall be considered more particularly to be a hypodermic device, i.e. a device designed to be positioned just beneath the patient's skin, although said device 1 can if necessary be implanted at other places in the patient's body and at a deeper level without departing from the scope of the invention.

According to the invention, the device 1 comprises a casing 6 whose wall 3 demarcates a chamber 2 which is designed to receive the fluid substance that is injected or collected.

The wall 3 of the casing 2 is pierced with at least one first access orifice 7 which is positioned so as to enable a needle 5, designed to inject or remove fluid substance into or from the chamber 2, to go through said wall 3 in crossing said first access orifice 7 until it penetrates the chamber 2.

Naturally, the access orifice 7 is associated with a self-sealing element 4 so as to form an area of a portion penetrable by the needle and designed to provide for the imperviousness of the device 1 both when it is penetrated by the needle 5 and during the transfer of liquid and after the withdrawal of said needle 5.

Preferably, the self-sealing element 4 is formed by a septum made out of a self-sealing material capable of being perforated by the needle. The term "self-sealing material" refers to a material having intrinsic properties of elasticity which make it capable especially of automatically closing the hole caused in it by the piercing, after the needle is extracted.

In a particularly preferable way, said penetrable portion 4 is formed by a septum made of biocompatible elastomer such as silicone For the convenience of the description, here below the self-sealing element 4 will be identified with a septum.

According to an important characteristic of the invention, the first access orifice 7 has a staged structure 10 comprising:
 a guiding portion 11 designed to limit the angular play 8 of the needle 5 when said needle is engaged therein, about a predetermined reference direction of penetration (XX') oriented towards the chamber 2,
 a flared intake portion 12 that extends the guiding portion 11 and opens on to the external surface 3E of the wall 3, so that it can make the path of the incident needle converge towards the guiding portion 11 and enable the engagement of said needle 5 in said guiding portion 11.

Advantageously, the staged structure 10 according to the invention is capable of taking charge of any incident needle 5 that comes into contact with the external surface of the casing 6 at the intake portion 12 and of guiding said needle along an appropriate path, substantially parallel to the predetermined direction of penetration (XX').

More particularly, said staged structure 10 is capable of acting appreciably similarly to a funnel placed against the bevel of the needle 5, the intake portion 12 playing the role, as needed, of centering means in gradually making said bevel slide gradually, as and when it moves forward towards the chamber and under the penetration force imposed on the needle until the bevel comes to the entry of the guiding portion and gets engaged in this portion, said guiding portion 11 thereafter calibrating or even rectifying the path of the needle 5 and more particularly its angle of approach in order to make it substantially coincide with the reference direction of penetration (XX') and thus ensure its appropriate penetration into the chamber 2.

Naturally, the reference direction of penetration (XX') is chosen by construction so as to "point" from the first access orifice 7 to the chamber 2 and preferably substantially towards the center of the chamber 2 in order to ensure that a needle passing through said access orifice 7 and substantially following this reference direction (XX') does not meet any obstacle that could prevent it from penetrating the chamber 2 efficiently, i.e. especially at a depth sufficient to enable the transfer of fluid from or to said chamber.

Thus, the staged structure advantageously improves the reliability of operation of the site since any needle 5 going through the casing 6 by an access orifice 7 is sure of reaching the center of the chamber 2 without its being necessary to twist the needle 5 or repeat the piercing gesture.

Furthermore, in guiding the needle 5 towards the cleared zones of the septum 4 and the chamber 2, the invention prevents the bevel from abutting the walls of the casing 6 so as to press against the walls of the casing 6, thus limiting the risk of deterioration to itself or again the risk of tearing the septum 4 through the extraction of the bent needle.

Preferably, the predetermined reference direction of penetration (XX') is substantially normal to the external face 3E and to the internal face 3I of the wall 3, said wall 3 furthermore preferably having a substantially constant thickness e.

Preferably, as illustrated in FIG. 2, the wall 3 is made out of a perforation-resistant material and covers the septum 4, i.e. it is situated appreciably opposite the chamber 2 relatively to the septum so as to get interposed between the septum and the exterior of the device 1.

Advantageously, such an arrangement makes it possible firstly to protect the septum from external aggression, especially abrasion phenomena, but also to ensure that the only possible access to the chamber 2 is obtained through the access orifices 7 duly designed for this purpose, enabling the penetration path (YY') of the needle 5 to be controlled.

The casing 6 and more particularly the wall 3 can advantageously constitute a protection structure capable of preserving the physical integrity of the device and especially that of the septum 4.

Furthermore, the wall 3 is preferably rigid, or at least more rigid than the septum 4 so as to form a bearing structure of an exoskeleton type, capable of giving the site, and especially a chamber 2, their functional shape and volume.

Said wall 3 will preferably be made as one piece out of a material that is preferably biocompatible and very preferably made of titanium, polycarbonate (PC), poly-ether-ether-ketone (PEEK), poly-sulfone (PSU) or any other appropriate material.

Preferably, the guiding portion 11 and/or the intake portion 12 have a substantially circular cross-section though it is possible to envisage the implementing of other shapes of sections such as curves or polygons.

Preferably, the intake portion 12 will extend from an inlet mouth 13 open on the external surface 3E of the wall and get gradually narrower as and when it approaches the chamber 2 until a neck 14 whose cross-section has a surface area smaller than that of the cross-section of the inlet mouth 13.

Preferably, the cross-section of the intake portion 12 has an even shape, for example a circular shape, with a cross-dimension (diameter) that decreases between the inlet mouth 13 and the neck 14.

According to an embodiment corresponding to FIGS. 1 to 8, the intake portion 12 is formed by a truncated cone with substantially rectilinear slopes 15.

According to another alternative embodiment illustrated in FIG. 9, the intake portion 12 is formed by a horn whose slopes 16 are appreciably outwardly curved.

Preferably, the angular aperture $\alpha_{11}$ of the guiding portion 11 is smaller than the angular aperture $\alpha_{12}$ of the intake portion 12.

In other words, the angle at the vertex defining the "conicity" if any of the guiding portion 11 is advantageously restricted as compared with that of the intake portion 12 in such a way that said intake portion can "capture" the needle 5 on an extended area of the external surface 3E of the wall, in this case on the entire surface of the inlet mouth 13 while the guiding portion 11 more strictly limits the transversal play of the needle 5 in order to prevent it from taking any path that may be deemed to be unsuitable.

Preferably, the angular aperture $\alpha_{12}$ of the intake portion 12 will range substantially from 60° to 120° and will preferably be substantially in the region of 90°. This corresponds substantially to slopes 15 beveled from 15 between 30° and 60° and preferably be substantially in the region of 45°, respectively.

According to one preferred embodiment, the guiding portion 11 is formed by a substantially straight cylinder, i.e. a cylinder whose walls are substantially rectilinear and parallel to the reference direction of penetration (XX') in such a way that its angular aperture $\alpha_{11}$ is appreciably zero as is shown in FIGS. 1 to 9.

In a particularly preferred way, the guiding portion will thus extend along a straight cylinder with a constant cross-section from the neck 14 up to an outlet mouth 17 opening onto the internal surface 31 of the wall 3.

Preferably, the intake portion 12 and the guiding portion 11 are substantially coaxial, directly attached to one another by the neck 14 and advantageously aligned along the reference direction of penetration (XX').

Preferably, with the device 1 being designed for use with needles 5 having a predefined diameter D0, the diameter $d_{11}$ of the guiding portion appreciably ranges from 1.2 times to twice said predefined diameter D0 and is preferably close to 1.5 times to 1.6 times said predefined diameter D0.

Thus, a guiding effect is obtained for the needle with a play that is necessary and sufficient to enable both the alignment of the needle substantially in the reference direction of penetration (XX') and the "floating" progress of said needle 5 without impact or deformation.

Naturally, the device 1 of the invention will be adapted to one or more of the standard formats of hollow needles used for the corresponding application and the sizing, especially of the diameter, of the access orifices 7 will naturally be determined accordingly.

In particular, the present invention also pertains as such to a medical kit comprising firstly at least one device 1 according to the invention and secondly a set of hollow needles 5 with a diameter D0 adapted to said device 1.

In this respect, the device 1 could be provided with a marking, possibly embossed and/or radio-opaque, enabling the practitioner immediately, before and/or after implantation, to recognize the hollow needle formats compatible with the said device 1.

Besides, in order to provide for an appropriate guiding range, i.e. in order to "close" the angular play δ measured relatively to the reference direction of penetration (XX'), which is still accessible to the needle 5 when it is engaged in the guiding portion 11, the length $L_{11}$ of said guiding portion 11 is preferably greater than or equal to 0.6 times its maximum length and as it happens 0.6 times its diameter $d_{11}$ as illustrated especially in FIG. 8.

The term "length" especially designates the size of the portion concerned measured between the opposite ends of said portion substantially along the reference direction of penetration (XX'), i.e. especially in a direction substantially normal to the internal and external surfaces of the wall 3 in the sense of the thickness of this wall 3.

More generally, the guiding portion 11 will be preferably laid out so that, once the needle 5 has gone through said guiding portion 11, the maximum angular divergence δ possible between the effective direction (YY') of the needle 5 and the reference direction of penetration (XX'), as illustrated in FIG. 8, is smaller than or equal to 35°, preferably smaller than or equal to 30°, and in a particularly preferred manner smaller than or equal to 25° or even substantially equal to 20°.

Furthermore, the length $L_{11}$ of the guiding portion 11 preferably amounts to about 60% to 70%, namely about two-thirds of the thickness e of the wall 3.

Furthermore, the length $L_{12}$ of the intake portion preferably represents about 40% to 60% of the length $L_{11}$ of the guiding portion 11 and preferably about 50% (half) of it.

Thus, the access orifice 7 could advantageously include two truncated sections joined together one after the other, namely with a first variably-sectioned truncated section corresponding to the intake portion 12 and a second constant-sectioned truncated section corresponding to the guiding portion 11, the second (guiding) truncated section having a length substantially equal to twice the length of the first (intake) section and thus substantially representing two-thirds of the thickness e of the wall 3.

According to a preferred alternative embodiment, the wall 3 is pierced with at least one second access orifice 107 which also has a staged structure 110 comprising a guiding portion 111 and an intake portion 112.

Preferably, the first and second access orifices 7, 107 are adjoining in such a way that their respective intake portions 12, 112 interfere at the external surface 3E of the wall 3.

In other words, the access orifices are placed side by side and close enough to each other for their respective intake portions 12, 112 to be secant and to define a common ridge-type boundary 20.

Said ridge 20 can correspond especially to a crest line forming a culminating point at the junction of the slopes 16, 116 of two horn-shaped intake portions which are substantially tangential to the external surface 3E of the wall.

Preferably, the ridge 20 however corresponds to a break in a protruding slope, i.e. a marked discontinuity of curvature between the slope 15 of the first hole 7 and the slope 115 of the neighboring hole 117.

Thus, any needle 5 coming to the common boundary of two access orifices 7, 107 will tip into either of said orifices without any risk of remaining blocked at the external surface 3E of the wall.

The ridge 20 thus forms so to speak the stem of the solid zones 21, resistant to perforation, which connect the access orifices 7, 107 to one another and provide for the cohesion of the casing 6.

Naturally, the number of access orifices is in no way limited, the device 1 preferably comprising at least three access orifices 7, 107, 207 or even several tens of access orifices, preferably juxtaposed.

Furthermore, all the access orifices 7, 107, 207 are preferably substantially identical in shape, structure and dimensions and are differentiated only by their spatial arrangement with respect to the chamber 2.

In this respect, it is noteworthy that the device 1 may have a plurality of access orifices 7, 107, 207 that are ordered in such a way as to form a row and preferably arranged edge to edge at a substantially constant pitch.

Naturally, the wall 3 may be provided with several successive rows of access orifices, said rows being offset in a particularly preferred way with respect to one another so as to be quincunxially arranged.

Preferably, each row has a constant and identical pitch to that of the neighboring rows and is offset by the equivalent of a half-pitch relatively to the rows that immediately neighbor it.

In particular, it is thus possible to give the external surface 3E of the wall 3 a honeycomb structure where each alveolus is formed by an access orifice for which the contour of the inlet mouth 13 demarcated by the ridges 20 is substantially hexagonal.

It is thus advantageously possible to obtain an arrangement that optimizes the proportion of the external surface 3E of the wall that remains permanently "pierceable" by the needle 5 in minimizing the residual expanse of the solid zones 21.

Naturally, the geometry of the wall 3 as well as the expanse of the removal area with access orifices is in no way restricted.

In particular, the wall 3 could take the form of a substantially plane plate or screen attached to the septum 4 and parallel to it.

However, in one preferred alternative embodiment, the wall 3 has a shape that is on the whole convex relatively to the exterior of the device 1 and is pierced with a plurality of access orifices 7, 107, 207 each provided with a staged structure 10, 110, 210 comprising a guiding portion and an intake portion so as to permit access to the chamber 2 in a total angular sector greater than or equal to 90°, preferably greater than or equal to 180° and in a particularly preferable way appreciably equal to 360°.

In other words, the accumulated angular coverage of the removal area about the device 1 advantageously offers lateral access to said device in a wide variety of directions of approach of the needle 5 and preferably throughout the rim of the device 1.

The working of this site 1 is therefore unaffected by an overturning of said site 1 on itself.

The wall 3 preferably forms a hollow cylinder with a generator axis (ZZ').

The term "cylinder" in this case designates any solid piece obtained by the extrusion of a base surface along a preferably rectilinear generatrix.

Naturally, the geometry of the base surface is in no way restricted, and can be for example polygonal, elliptical or circular, having a constant or variable section along the generatrix.

In particular, the device 1 and especially the chamber 2 may, on the whole, have a generally straight cylindrical, ovoid, ellipsoid, pyriform or polyhedral.

Figure 3:
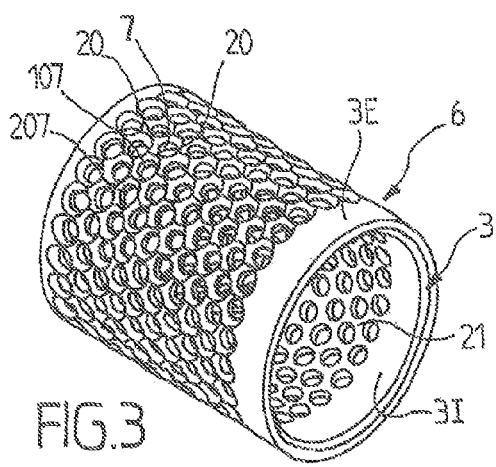
FIG. 3 is a view in perspective of a part of the casing implemented within the device shown in FIGS. 1 and 2.
Figure 4:
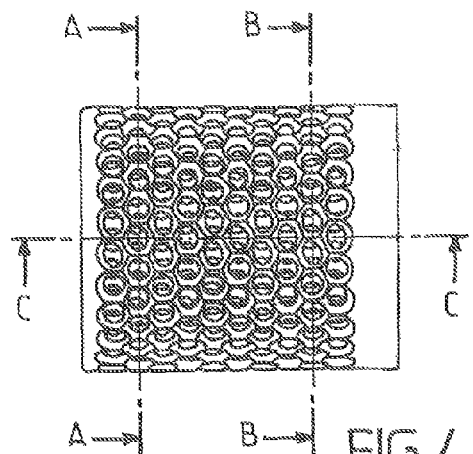
FIGS. 4, 5, 6, 7 and 8 represent views of the casing of FIG. 3 respectively in a side view, in a first cross-section, a second cross-section, in a longitudinal view and in a magnified detailed view in cross-section.
Figures 5, 6:
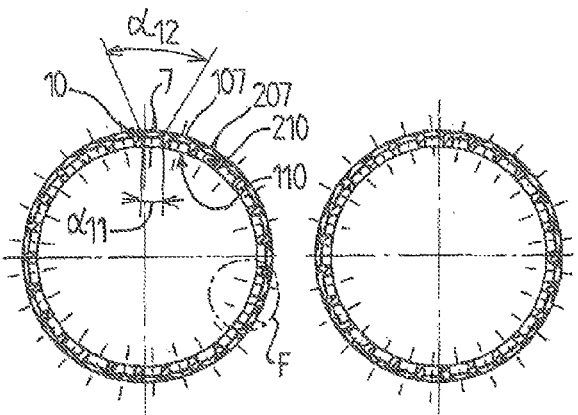
Figure 7:
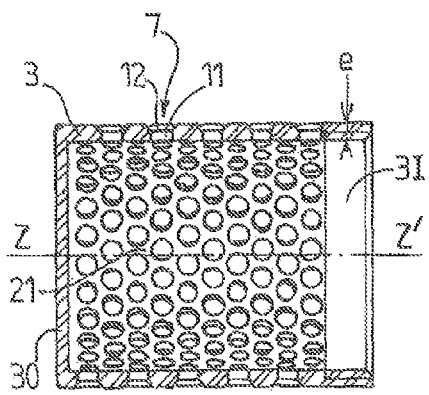

Preferably, the device 1 and more particularly the casing 6 and the wall 3 have, on the whole, a geometry of revolution about the generator axis (ZZ') and especially a circular cross-section as illustrated especially in FIGS. 1 and 3.

Advantageously, this feature gives the device 1 a relatively simple, compact, light and atraumatic structure.

According to a preferred alternative embodiment, the septum 4 forms a substantially cylindrical sleeve surrounding the chamber 2.

Advantageously, the septum, 4 is coaxial with the casing 6, the internal surface 3E of the wall 3 being superimposed on said septum 4 preferably substantially throughout its surface in appreciably matching the external contour of this surface.

Advantageously, the access orifices 7, 107, 207 may be substantially radial so that the reference direction of penetration (XX') associated with each of them converges substantially towards the generator axis (ZZ') which passes by the center of the chamber 2.

More particularly, the orifices can be arranged equidistantly in successive rings, said rings being stacked quincunxially along the generator axis (ZZ') so as to form an incurvated alveolate structure gripping the septum 4.

For example, the perforated tube shown in FIGS. 4 to 7 has 10 rows of 25 orifices each, the angular pitch being 14.40°.

Advantageously, the casing could be manufactured by machine-turning, the radial piercings being made by means of a staged drill so as to form the straight piercing corresponding to the guiding portion 11 and the conical milling corresponding to the intake portion 12 in a single pass.

Besides, the site 1 of the invention may comprise a first flange and a second flange 30, 31 which are preferably solid, rigid and perforation-resistant, designed to block the casing 6 at its ends on either side of the septum 4.

According to a preferred alternative embodiment, the first flange 30 forms one block with the open-worked side wall 3 of the casing 6 and is the bottom of said casing, which then takes the form of a blind-end shell.

Furthermore, the second flange 31 may be attached by being screwed into the casing 6 so that it can pre-stress the septum 4 in compression and more particularly in a direction substantially transversal to the reference direction of penetration (XX'), i.e. substantially along the generator axis (ZZ').

Advantageously, the intensity of this longitudinal compression is adjustable according to the degree of screwing in, hence of penetration within the casing 6, of the second flange 32.

The second flange 32 may be used as a support for a nozzle 33 used to connect the site to a catheter (not shown), said nozzle 33 being preferably centered relatively to the second flange 32 and aligned with the casing 6 and the sleeve 4 along the generator axis (ZZ').

Besides, the site 1 may include an anti-perforation shield 34 designed to prevent the needle 5 from crossing the chamber 2, and then the casing 6 from one side to the other.

In particular, it is possible to use a shield provided with rigid plates arranged in a star shape, for example a six-pointed star, positioned within the septum 4 substantially along the generator axis (ZZ').

Finally, the site 1 may comprise an external sheath 35 made for example out of silicone in order to complete the cladding and the atraumatic finish of said implantable site 1. The wall of the site 1 then has a multi-layered structure, the wall 3 being positioned between the external sheath 35 and the septum 4.

Furthermore, the septum 4 may also be pre-stressed in radial compression, i.e. substantially in the direction of the thickness of the wall 3, in setting up a force-fitting of said septum 4 in the casing 6, the internal surface 31 of the wall 3 then being supported on the entire external side face of the sleeve forming the septum 4, between the first and second flange, so as to prompt the elastic constriction and a radial pre-stressing of said sleeve.

Advantageously, the anti-perforation shield 34 may counter the centripetal radial shifting of the internal wall of the sleeve, i.e. firstly substantially maintain the functional volume of the chamber 2 in especially preventing the crushing of the sleeve during the introduction of the sleeve 5 and secondly improve the compressive effect of the septum 4 which is sandwiched between the wall 3 and said shield 34.

The imperviousness and longevity of the site 1 are thereby improved, including for the small thicknesses of the septum 4.

Moreover, the design of the device 1 according to the invention, in which the septum 4 is compressed both radially and longitudinally by a contraction, preferably of the order of 5% to 10% of its concerned dimensions (diameter and length respectively), makes it possible to compensate during assembly for manufacturing variations in terms of silicone quality, the hardness of which generally varies in the range of +/−5 Shore A in the same batch, or again in terms of dimensions of molded parts such as the septum 4.

It is thus possible to routinely assemble any septum 4 with any casing 6 without its being necessary to make a prior sorting out of these parts to ensure that they are compatible.

Purely by way of a non-restrictive indication, the device 1 of the invention may have substantially the following dimensions and proportions, in the particular case of a device adapted to a hollow needle with a diameter D0 equal to 0.9 mm:

- sleeve at rest (before compression): external diameter equal to 15 mm, wall thickness equal to 3.5 mm, length (measured along the generator axis) equal to 19 mm;
- pre-stressed assembled sleeve: external diameter equal to 14 mm, thickness equal to 3.35 mm, length equal to 17.5 mm;
- casing 6: overall length equal to 20.5 mm, internal diameter equal to 14 mm, wall thickness e of the wall 3 ranging from 0.8 mm to 2 mm and preferably in the region of 1.5 mm;
- piercing diameter $d_{11}$ of the orifices in the guiding portion 11 equal to 1.4 mm;
- intake portion 12: 0.4 mm×45° to 0.5 mm×45°;
- linear pitch of staging of the rows of holes: 3.20 mm for ten rows.

The working of a site 1 according to the invention shall now be briefly described with reference to the alternative embodiment illustrated in FIGS. 1 and 2.

When the needle coming from the exterior reaches the site 1, it first of all meets the external sheath 35 which it pierces through.

The needle 5 then comes against the external surface 3E of the wall at the inlet mouth 13 of an access orifice 7.

If the inlet point and the direction (YY') of the needle coincide substantially with the position and orientation of the corresponding guiding portion 11, then the needle continues its path and directly crosses the hole 7, possibly without even touching its wall, then meets the septum 4 which it pierces through and continues its onward progress until it reaches the chamber 2.

However, the inlet point and the incident direction of the needle 5 may be such that the bevel of each needle 5 abuts an inclined slope 15, 16 of the intake portion 12.

Under the thrust exerted by the practitioner, the needle then starts sliding along said slope 15, 16 pushing in through the intake portion 12.

In doing so, because the intake portion 12 converges towards the neck 14, the head of the needle 5 is gradually deflected substantially towards the center of the hole 7, as and when the bevel pushes into it.

The bevel then crosses the neck 14 and the needle 5 engages in the guiding portion 11.

If the direction of the needle (YY') exceeds the angular play δ authorized by said guiding portion 11, i.e. if its tilt is far too pronounced relatively to the reference direction (XX'), then the needle strikes against the internal wall of said guiding portion 11 which deflects its path in gradually turning it down towards the reference direction (XX').

The needle 5 is thus routed 11 within the guiding portion 11, substantially in parallel to the reference direction (XX'), and then emerges from said guiding portion 11 to then penetrate the thickness of the underlying septum 4.

After having successively crossed the two portions 12, 11 of the staged structure 10, it then crosses the septum 4 from one side to the other without meeting any obstacle and without remaining wedged in its thickness.

It then emerges from the septum to plunge freely into the cavity of the chamber 2.

The practitioner can then do the removal or the injection.

When the needle 5 gets withdrawn, the septum 4 automatically closes the hole that it has formed behind it so as to restore the imperviousness of the site.

It is noteworthy that the staged structure 10 according to the invention rectifies the trajectory of the needle 5 before said needle gets engaged in the septum 4, i.e. so long as it is still "floating" or at most "pierced" in the external envelope 35 which is particularly thin and flexible and therefore not likely to hinder the corrective movements.

The correction of the path may therefore be done upstream to the septum 4 before the perforation proper, finely and flexibly without any risk of bending the needle 5, compromising the imperviousness of the site 1 or tearing the septum 4.

The site 1 of the invention advantageously has a major piercing surface while maintaining a limited overall space requirement and secures the piercing gesture by guiding the practitioner without ever excessively stressing the needle.

Said site 1 is moreover particularly tolerant to directions of piercing and capable of self-correcting the path of the incident needles so as to ensure that they effectively reach the chamber. The result of this is greater comfort of use both for the practitioner and for the patient.

The invention claimed is:

1. Implantable medical device for injecting and/or removing a fluid substance into and/or from a human or animal organism, said device comprising a casing whose wall demarcates a chamber designed to receive said fluid substance, the wall of the casing being pierced with at least one first access orifice positioned to enable a needle designed for injecting or removing the fluid substance into or from the chamber to go through said wall by crossing said first access orifice, wherein the first access orifice has a staged structure comprising:

a guiding portion designed to limit the angular play of the needle when said needle is engaged therein, around a predetermined reference direction of penetration oriented towards the chamber so that the maximum angular divergence between the direction of the engaged needle and the reference direction of penetration is smaller than or equal to 35°, a flared intake portion that extends the guiding portion and opens on to the external surface of the wall so that it can make the path of the incident needle converge towards the guiding portion and enable the engagement of said needle in said guiding portion.

2. Device according to claim 1, wherein the wall is made out of a perforation-resistant material and covers a septum made out of a self-sealing material penetrable by the needle, of the silicone type.

3. Device according to claim 1, wherein the wall is pierced with at least one second access orifice which also has a staged structure comprising a guiding portion and an intake portion and in that the first and second access orifices are adjoining in such a way that their respective intake portions interfere at the external surface of the wall.

4. Device according to claim 1, wherein the angular aperture of the guiding portion is smaller than the angular aperture of the intake portion.

5. Device according to claim 1, wherein the guiding portion is formed by a substantially straight cylinder.

6. Device according to claim 1, wherein the intake portion is formed by a truncated cone with substantially rectilinear slopes.

7. Device according to claim 1, wherein the intake portion is formed by a horn whose slopes are substantially outwardly curved.

8. Device according to claim 1, wherein the guiding portion and/or the intake portion have a substantially circular cross-section.

9. Device according claim 8, wherein the device being designed for use with needles having a predefined diameter, the diameter of the guiding portion substantially ranges from 1.2 times to twice said predefined diameter.

10. Device according to claim 1, wherein the length of the guiding portion is greater than or equal to 0.6 times its width.

11. Device according to claim 1, wherein the length of the guiding portion amounts to about 60% to 70% of the thickness of the wall.

12. Device according to claim 1, wherein of the intake portion represents about 40% to 60% of the length of the guiding portion.

13. Device according to claim 1, wherein the wall has a shape that is on the whole convex relatively to the exterior of the device and in that said wall is pierced with a plurality of access orifices each provided with a staged structure comprising a guiding portion and an intake portion so as to permit access to the chamber in a total angular sector greater than or equal to 90°.

14. Device according to claim 13 wherein the wall forms a cylinder with a generator axis and in that the access orifices are substantially radial.

15. Device according to claim 1 wherein it comprises a plurality of adjoining access orifices, laid out in a plurality of staged rows, offset relatively to one another in such a way that the external surface of the wall has a honeycomb structure.

16. Device according claim 1, wherein the wall is made in one piece.

* * * * *